(12) United States Patent
Froom

(10) Patent No.: US 6,637,266 B1
(45) Date of Patent: Oct. 28, 2003

(54) NON-DESTRUCTIVE INSPECTION, TESTING AND EVALUATION SYSTEMS FOR INTACT AIRCRAFT AND COMPONENTS AND METHOD THEREFORE

(76) Inventor: Douglas Allen Froom, 9512 Buffalo Ave., Orangevale, CA (US) 95662

( * ) Notice: Subject to any disclaimer, the term of this patent is extended or adjusted under 35 U.S.C. 154(b) by 0 days.

(21) Appl. No.: 10/081,900

(22) Filed: Feb. 20, 2002

Related U.S. Application Data

(62) Division of application No. 09/645,540, filed on Aug. 25, 2000, now Pat. No. 6,378,387.

(51) Int. Cl.<sup>7</sup> ............................................. G01N 29/04
(52) U.S. Cl. ....................................................... 73/583
(58) Field of Search ................................. 73/1.79, 1.81, 73/588, 598, 600, 583, 865.8; 378/58, 62, 64; 701/29, 30, 32, 33, 35; 324/228, 237, 238, 240–242

(56) References Cited

U.S. PATENT DOCUMENTS

| | | | |
|---|---|---|---|
| 4,685,966 A | * | 8/1987 | Garner et al. .................. 73/583 |
| 4,715,228 A | * | 12/1987 | Livsey et al. .................. 73/583 |
| 5,111,402 A | | 5/1992 | Brooks et al. |
| 5,170,352 A | | 12/1992 | McTamaney et al. |
| 5,987,960 A | | 11/1999 | Messner et al. |
| 6,003,808 A | | 12/1999 | Nguyen et al. |
| 6,220,099 B1 | * | 4/2001 | Marti et al. |

* cited by examiner

*Primary Examiner*—Robert Raevis
(74) *Attorney, Agent, or Firm*—Bernhard Kreten

(57) ABSTRACT

A non-destructive inspection, testing and evaluation system and process is provided for the review of aircraft components. The system provides for a structure configured to contain an inspection and testing apparatus and the aircraft components under inspection. The structure is lined with shielding to attenuate the emission of radiation to the outside of the structure and has corbels therein to support the components that constitute the inspection and testing apparatus. The inspection and testing apparatus is coupled to the structure, resulting in the formation of a gantry for supporting a carriage and a mast is mounted on the carriage. The inspection and testing equipment is mounted on the mast which forms, in part, at least one radiographic inspection robot capable of precise positioning over large ranges of motion. The carriage is coupled to the mast for supporting and allowing translation of the equipment mounted on the mast. The mast is configured to provide yaw movement to the equipment.

22 Claims, 11 Drawing Sheets

NON-DESTRUCTIVE INSPECTION, TESTING AND EVALUATION SYSTEMS FOR INTACT AIRCRAFT AND COMPONENTS AND METHOD THEREFORE

This application is a divisional of application Ser. No. 09/645,540, filed Aug. 25, 2000, now U.S. Pat. No. 6,378,387, issued Apr. 30, 2002.

This invention was made in the performance of a cooperative research and development agreement with the Department of the Air Force. This invention may be manufactured and used by or for the Government of the United States for all government purposes without the payment of any royalty.

FIELD OF THE INVENTION

The following invention is generally related to instrumentalities and methodologies for the non-destructive inspection, and especially for testing and evaluation of aircraft components.

BACKGROUND OF THE INVENTION

Recent tragedies in aircraft transportation have caused concern over the ability of airlines to evaluate the airworthiness of aircraft within their respective fleets. As airframes age, the characteristics of the materials that constitute the airframe components change due to the stresses and strains associated with flights and landings. The material goes beyond the point of elasticity (the point the material returns to its original condition) and into the point of plasticizing or worse, beyond to failure. As a result, inspections and testing are conducted on aircraft components periodically during the aircraft's component life cycle as are mandated by governing bodies and based largely on empirical evidence.

Current commercial industry inspection and repair methods are inefficient, costly and not standardized. Their inspection and repair procedures and processes have changed little in the past 20 or 30 years and have not solved the "Aging Aircraft" safety problems. Inspection of aircraft components are historically limited to the "Tap Test," visual inspection, and Eddy Current analysis. Standardized technical repairs are nonexistent. Commercial safety integrity is continually compromised by not determining the extent of aircraft structure corrosion and fatigue.

Unfortunately, manned inspection is still the state of the art. Inspection timetables are developed and updated primarily as a function of anecdotal evidence, all too frequently based on airline catastrophes.

Inspections and testing are bificurated into two areas: destructive testing and nondestructive inspection (NDI), nondestructive testing (NDT) or nondestructive evaluation (NDE). The area of destructive testing, as the name implies, requires the aircraft component under scrutiny to be destroyed in order to determine the quality of that aircraft component. This can result in a costly endeavor because the aircraft component is destroyed even though it passed the test procedure. It is, therefore, no longer available for use. Frequently, where destructive testing is done on samples (e.g. coupons) and not on actual components, the destructive test may or may not be reflective of the forces that the actual component could or would withstand within the flight envelope of the aircraft.

On the other hand, NDI, NDT or NDE have the obvious advantage of being applicable to actual aircraft components in their actual environment. Several important methods of NDI, NDT or NDE that are performed in a laboratory setting are listed and summarized below.

Radiography. This is a general term for the inspection of a material by subjecting it to penetrating irradiation. X-rays are the most familiar type of radiation used in this technique, although good damage detection has been done using neutron radiation. Most materials used in aircraft component manufacturing are readily acceptable to X-rays. In some instances, an opaque penetrant is needed to detect many defects. Real-time X-rays are starting to be used to permit viewing the area of scrutiny while doing the procedure. Some improvement in resolution has been achieved by using a stereovision technique where the X-rays are emitted from dual devices which are offset by about 15°. When viewed together, these dual images give a three-dimensional view of the material. Still, the accuracy of X-rays is generally no better than +10% void content. Neutrons (N-ray), however, can detect void contents in the +1% range. The difficulty is the obvious problem with safety and radiation sources. addition to the normal use to detect internal flaws in the metals and composite structures, X-rays and neutrons can detect misalignment of honeycomb cores after Ultrasonics. This is most common method for detecting flaws in composite materials. The method is performed by scanning the material with ultrasonic energy while monitoring the reflected energy for attenuation (diminishing) of the signal. The detection of the flaws is somewhat frequency-dependent and the frequency range and scanning method most often employed is called C-scan. In this method, water is used as a coupling agent between the sending device and the sample. Therefore, the sample is either immersed in water or water is sprayed between the signal the signal transmitter and the sample. This method is effective in detecting defects even in thick samples, and may be used to provide a thickness profile. C-scan accuracies can be in the +1% range for void content. A slightly modified method called L-scan can detect stiffness of the sample by using the wave speed, but this method requires that the sample density be known.

Acousto-ultrasonics. This analysis method is similar to ultrasound except that separate sensors are used to send the signal and other sensors are used to receive the signal. Both sensors are, however, located on the same side of the sample so a reflected signal is detected. This method is more quantitative and portable than standard ultrasound.

Acoustic emission. In this method, the sounds emitted by a sample are detected as the sample is subjected to a stress. The stress can be mechanical, but need not be. In actual practice, in fact, thermal stresses are the most commonly employed. Quantitative interpretation is not yet possible except for well-documented and simple shapes (such as cylindrical pressure vessels).

Thermography. This method, which is sometimes called IR thermography, detects differences in the relative temperatures of the surface and, because these temperature differences are affected by internal flaws, can indicate the location of those flaws. If the internal flaws are small or far removed from the surface, however, they may not be detected. Two modes of operation are possible-active and passive. In the active mode, the sample is subjected to a stress (usually mechanical and often vibrational) and then the emitted heat is detected. In the passive mode, the sample is externally heated and the thermal gradients are detected.

Optical holography. The use of laser photography to give three-dimensional pictures is called holography. This method can detect flaws in samples by employing a double-image method where two pictures are taken with an induced stress in the sample between the times of the pictures. This method has had limited acceptance because of the need to isolate the camera and sample from vibrations. Phase locking may eliminate this problem. The stresses that are imposed on the sample are usually thermal. If a microwave source of stress is used, moisture content of the sample can be detected. For composite material, this method is especially useful for detecting debonds in thick honeycomb and foam sandwich constructions. A related method is called shearography. In this method, a laser is used with the same double exposure technique as in holography with a stress applied between exposures. However, in this case an image-shearing camera is used in which signals from the two images are superimposed to give interference and thereby reveal the strains in the samples. Because strains are detected, the size of the pattern can give an indication of the stresses concentrated in the area and, therefore, a quantitative appraisal of the severity defect is possible. This attribute, plus the greater mobility of this method over holography, and the ability to stress with mechanical, thermal, and other methods, has given this method wide acceptance since its introduction.

Even though there are a wealth of diagnostic tools, there is a need to provide systems and principled processes to execute NDI, NDT and NDE of aircraft and their constituent components to take advantage of the methods briefly described above in order to better characterize the material properties of materials used in the manufacturing of aircraft components. The present invention fulfills this need outside of a laboratory setting.

The present invention includes three robotic imaging inspection methods and technologies: real-time X-ray, N-ray and laser ultrasonics. When used separately, certain imaging inspection methods find certain aircraft structural defects. For example, the present invention's N-ray imaging inspection methodology locates corrosion and measurable loss of structural material. The present invention's real-time X-ray imaging inspection methodology can find the smallest of structural cracks; while the ultrasonics methodology locates defects regardless of a composite or metal structure's configuration. When used in combination on any given aircraft or component, all structural defects and discrepancies can be located within high precision and trend analysis of future defect problems per model and series aircraft can be formulated and determined.

The following citations reflect the state of the art of which applicant is aware and are included herewith to discharge applicant's acknowledged duty to disclose relevant prior art. It is stipulated, however, that none of these citations teach singly nor render obvious when considered in any conceivable combination the nexus of the instant invention as disclosed in greater detail hereinafter and as particularly claimed.

| PATENT NO. | ISSUE DATA | INVENTOR |
| --- | --- | --- |
| 6,003,808 | Dec. 21, 1999 | Nguyen, et al. |
| 5,111,402 | May 5, 1992 | Brooks, et al. |

SUMMARY OF THE INVENTION

The present invention is directed to systems and processes that perform NDI, NDT and NDE on aircraft in whole and for components individually. One key to the present invention involves systematic, automated inspection coupled with comparison to a standard.

The term "aircraft components" encompasses, but not limited to: items as small as individual fasteners, pieces, sections or strands of wiring, materials, fasteners once installed and in their environment, weld seams, sections of panels, mounts and brackets, control surfaces, landing gear, the components and pieces thereof; flight surfaces, components and pieces thereof; a powerplant, its sections, its components and pieces thereof; sections of a fuselage and its entirety; to the whole aircraft positioned in an inspection bay or hangar.

NDI, NDT or NDE systems and processes having the characteristics of the present invention constitute a structure, preferably configured as an enclosure, to contain an inspection and testing apparatus and the aircraft components under inspection. The structure is lined with shielding to attenuate the emission of radiation to the outside of the enclosure and having corbels therein to support the components that constitute the inspection and testing apparatus. The inspection and testing apparatus is coupled to the structure, resulting in the formation of a gantry for supporting a carriage and a mast mounted on the carriage. An electromagnetic radiation emitter, electromagnetic radiation detector or both are mounted on the mast, which forms, in part, at least one radiographic inspection robot capable of precise positioning over large ranges of motion. The carriage is coupled to the mast for supporting and allowing translation of the at least one electromagnetic radiation emitter and detector mounted on the mast, wherein the mast is configured to provide two axes of movement of the electromagnetic radiation emitter, detector or both.

The emitter, detector or both is configured to provide rotation about at least one axis of pitch, roll and yaw motion of the emitter, detector or both.

Such NDI, NDT or NDE systems and process are preferably configured wherein the emitter, detector or both are configured as a yoke to provide rotation about at least one axis of pitch and roll motion of the emitter, detector or both. The yoke could include first and second members capable of adjusting the distance between the members; whereby the first member supports a source of electromagnetic radiation and the second member supports at least one of an electromagnetic radiation detector or an imaging device.

An NDI, NDT or NDE system or process having the characteristics of the present invention preferably contains the steps to perform the method for the non-destructive inspection and testing of aircraft components including a database comprising at least one profile of a prototypical aircraft component, maintaining an enclosure at constant environmental conditions, placing at least one aircraft component into the enclosure and allowing sufficient time to permit the aircraft component to reach the constant environmental conditions, precisely placing reference markers on specific areas of the aircraft component, reading the location of the reference markers, comparing the reading with the at least one profile and reporting the result of the comparison. The reference markers introduce the aircraft to the system and can uncover gross distortions in the aircraft's geometry, and aircraft location.

Further characteristics of the present invention include a gantry robot having a yoke to which an attached scanning apparatus provides the capability to reposition the yoke and scanning apparatus without the need for disassembly. The joints of the yokes are configured so as to be capable of articulation such that each leg of the yoke may be raised or lowered. By allowing each leg of the yoke to be raised or lowered, the scanning apparatus may be used to scan areas of an intact aircraft that would otherwise be difficult or impossible to scan.

As previously stated the present invention has one or more robots. The use of multiple robots provides several advantages. Firstly, multiple robots allow simultaneous inspection of several areas of an aircraft, thereby reducing the time required to inspect an aircraft. Secondly, multiple robots avoid the need for a single long supporting beam, which would reduce positioning accuracy and repeatability. Thirdly, multiple robots allow each robot to be specifically designed to inspect particular areas of an aircraft, thereby allowing accommodation of special attributes of the various areas.

A structure is provided to contain inspection apparatus and items under inspection and defines an enclosure. The structure comprises walls, a ceiling, and a floor. A hanger door entrance is defined in a wall. The hanger door entrance is equipped with a hanger door. The walls, ceiling, and hanger door are designed to attenuate x-ray radiation and neutron radiation.

Corbels are provided to support multiple robots. The walls, ceiling, and hanger door entrance are designed to support the corbels, which provide x-axis translation. The structure is designed to accommodate structural loading while maintaining accuracy and repeatability of robot position over six axes of movement within a narrow range of tolerances better than ±0.250 inches, and preferably better than ±0.160 inches. The structure accommodates structural loading of various types, for example floor loading, wind loading and loading from the mass of the robots.

One embodiment of the invention includes a plurality of carriages on a single beam. For example, one carriage may provide support and translation of a robot for n-ray radiography, and another carriage may provide support and translation for a robot for x-ray radiography.

The inspection facility is designed to protect personnel from radiation hazards (including X-rays and neutrons). Shielding, including shielding of walls, doors, and windows is provided. Interlocks are provided to prevent the emission of radiation when personnel might be endangered, such as when a door is opened. Other measures, such as key controls and password authentication are provided to prevent emission of radiation or other potentially hazardous activities, such as motion of robotic systems, without approval of authorized personnel. Radiation monitoring and alarm systems are provided to detect abnormal radiation levels and provide warning.

One example of a technique used to provide shielding is the penetration shielding areas (for example, walls, doors, floors, ceilings, windows, etc.) at an angle sufficient to ensure that any radiation substantially perpendicular to the plane of the shielding material will be incident upon the shielding material of which the shielding area is constructed. This technique avoids the need to add additional shielding material, such as by packing a perpendicularly bored hole with additional shielding material.

A method for design of a non-destructive inspection, testing, and evaluation system for aircraft and components having a precision robotic system is provided. The dimensional and structural requirements of a building are determined, and a preliminary design for the building is made. The preliminary design for the building is analyzed to identify any frequencies at which such a building might resonate. For example, a technique such as finite element analysis may be employed. Based on the results of the analysis, the preliminary design of the building may be modified to correct any deficiencies.

The dimensional, structural, and functional requirements for robots to be housed within the building are determined, and a preliminary design of the robots is made. The preliminary design of the robots is analyzed to identify any frequencies at which such robots might resonate. Any interaction between the resonant frequencies of the building and the resonant frequencies of the robot are analyzed. Based on the results of the analysis, the preliminary design of either or both of the building and the robots may be modified to correct any deficiencies.

The dimensional, structural, and functional requirements of any end effectors mounted on the robots are determined, and a preliminary design of the end effectors is made. The preliminary design of the end effectors is analyzed to identify any frequencies at which such end effectors might resonate. Any interruption between other elements, such as the building or the robots, is analyzed. Based on the results of the analysis, the preliminary design of any or all of the building, robots, or end effectors may be modified to correct any deficiencies.

Another factor to be considered is the type of earthquake region in which the facility is to be located. Different earthquake regions may exhibit earthquakes having different characteristics, for example earthquakes having vibration and motion of predominantly a certain frequency range. This frequency range is determined for the location at which the facility is to be located based on geological data. The preliminary designs of the building, robots, and end effectors is analyzed base on anticipated excitation from earthquakes. Based on the results of the analysis, the preliminary design of any or all of the building, robots, or end effectors may be modified to correct any deficiencies.

When the preliminary designs of the buildings, robots, and end effectors are completed, modeling of the entire system may be performed to assure accuracy and repeatability of robot positioning. Oscillatory excitation of the system components resulting from robot motion and acceleration and deceleration may be analyzed. Designs of the system components may be modified to maximize desirable characteristics, such as accuracy and repeatability of robot positioning, while minimizing undesirable characteristics, such as unwanted oscillatory excitation of system components.

The major assemblies of the non-destructive inspection and testing structure are the structure itself, preferably a building and further defining an enclosure, and the inspection and testing apparatus. A structure is provided to contain the inspection and testing apparatus and the items under inspection or testing. The structure is preferably composed of walls, floor, a ceiling and a hanger door. The walls, ceiling and hanger door are designed to attenuate X-ray radiation and neutron radiation. Corbels are provided to support the multiple robots. The walls, ceiling and hanger door entrance are designed to support the corbels thus permitting translation across the items under inspecting, testing or evaluation. The structure is designed to accommodate structural loading while maintaining accuracy and repeatability of the robot positions, i.e., the inspection and testing apparatus over six axes of movement within a narrow range of tolerances better than plus or minus 0.25 inches and preferably better than plus or minus 0.16 inches. The structure accommodates structural loading of various types, for example, floor loading, wind loading and loading from the mass of the robot.

The non-destructive inspection and testing system for aircraft components is capable of precise positioning over large ranges of motion. The non-destructive inspection and testing system for aircraft components comprises a beam arrangement for supporting and allowing translation of a carriage. The beam is mounted on rails which are attached to the facility corbels by the means of end trucks, providing movement along the length of the facility or X axes. The carriage moves along the length of the beam providing Y axes, and a telescoping tube or mast is attached to the carriage in a vertical position, providing Z axes. At the bottom of the mast, three axes of movement are provided: pitch, rotate, and yaw of the yoke to which the inspection apparatus is attached. The translations permit the system to scan the intact aircraft to the component level. The carriage is coupled to a mast structure for supporting and allowing translation of a yoke. The mast comprises a plurality of tubes that can move telescopically to provide a large range of motion in a vertical direction while supporting large amounts of mass. In one embodiment of the invention, the beam arrangement is located overhead, for example, near the ceiling of the building. The building and beam arrangement form a gantry for supporting the carriage and structure as well as the yoke which is mounted on the mast. In the preferred embodiment the yoke includes two members that may be extended for example telescopically to adjust the throat depth of the yoke. Also, one embodiment of the yoke is configured to accommodate surfaces that change the camber of the wing. In particular configurations the first member supports a beam source and the second member supports an imaging device. In an alternative embodiment the mast supports a laser ultrasonic scanner. This laser ultrasonic scanner is attached to the mast of the inspection and testing apparatus and configured with rotational axes to allow scanning in a plurality of directions across complex surfaces of the aircraft or aircraft components.

Real-time X-ray radiography is accomplished in motion utilizing multi-axis movement of robots to scan at the rate of one to three inches per second and at three to five times magnification. Any pendulum or sway effect at the bottom of the mast (with yoke attached) causes the real-time radiography image to be un-focused, distorted and unreadable to the operator. The problematic pendulum or sway effect is caused by two separate resonating frequencies: the first is the fundamental frequency of the robot based upon the mass and rigidity of the robot structure; and the second is the robot mounting to the housing facility, which has its own resonating frequency when the robot is in motion or multiple robots are in motion or working. Providing two separate parallel bridges mounted to single end trucks with carriage straddling both parallel bridges and the mast located between the two separate bridges yields acceptable results so long as the length of the bridge does not exceed a certain length, typically fifty feet. Providing a single rail bridge typically permits a length of the bridge not to exceed ninety-six feet.

Existing hangar structure would have to be modified or new facilities would have to be built to attenuate any pendulum effect and resonating frequencies that could distort robotic inspection readings. Facility modification or new design would be based upon three separate requirements: seismic; resonant frequency of the facility with the robots in motion and the robotic envelope. Site surveys would determine the seismic activity, ground water location, type of soil, soil compaction and would result in building the facilities foundation as an isolation pad. The resonant frequency of the facility with the robots in static positions is modeled to evaluate the pendulum effect of the robots and to determine the amount of reinforcement of steel and concrete needed to meet frequency requirements for the facility's bearing walls. At issue is the facility's hangar door. As the robots are moved closer to the hangar door, the pendulum effects become unacceptable. Therefore, modifications to the hangar door are needed: a steel and concrete header is provided above the door, while below ground level, a lateral tie or footer is provided. Such modifications rigidify the side of the structure containing the hangar door to attenuate any resonant frequencies to acceptable levels for the inspection of aircraft with the robots. The robot envelope is determined by the type of aircraft that would be inspected within the facility. The envelope is factored in and any resonant frequencies are attenuated in order to provide inspection accuracy and repeatability.

Inspection of aircraft wings require the control surfaces to be extended to allow for a total wing inspection. This wing configuration causes sharp radial surface turns at the fore and aft ends of the wings' leading and trailing edge surfaces and the inability for a normal "C" shaped yoke to conform to these areas to perform a total inspection perpendicular to the part under inspection. The solution to this problem is to provide a modified "C" shaped yoke with the lower arm having an articulating member, akin to a double joint, in order to allow the lower arm to tuck underneath the control surface.

Further characteristics of the present invention include a gantry robot having a yoke to which an attached scanning apparatus provides the capability to reposition the yoke and scanning apparatus without the need for aircraft disassembly. The joints of the yoke are gimbaled, so as to be capable of articulation, such as each leg of the yoke allows both sender and receiver to maintain perpendicular alignment to each other. By allowing each leg of the yoke to be raised or lowered, the scanning apparatus may be extended, used to scan areas of an intact aircraft that would otherwise be difficult or impossible to scan. Yoke configuration also includes telescoping legs to allow the throat depth to change. This change in depth is needed to reach points on an aircraft's wing where the wing root may exceed 27 feet and where the outer part of the wing is approximately four feet across.

OBJECTS OF THE INVENTION

Accordingly, it is a primary object of the present invention to provide a new, novel and useful Non-Destructive Inspection, Testing and Evaluation System for Intact Aircraft and Components and method therefore.

It is a further object of this invention to provide a method and apparatus as characterized above which accurately forecasts the need for corrective measures in a timely manner.

It is a further object of this invention to provide a method and apparatus which is easy to use and minimize the need for highly experienced personnel.

It is a further object of this invention to provide a method and apparatus where the diagnosis is repeatable.

It is a further object of this invention to provide a method and apparatus where the system and method can be reliably replicated.

It is a further object of this invention to provide a method and apparatus where the results from individual inspectors can be subsequently incorporated into a trend analysis data base.

It is a further object of this invention to provide a method and apparatus where the analysis does not mandate destruction of the item examined.

These and other objects will be made manifest when considering the following detailed specification when taken in conjunction with the appended drawing figures.

DESCRIPTION OF PREFERRED EMBODIMENTS

Figure 1:
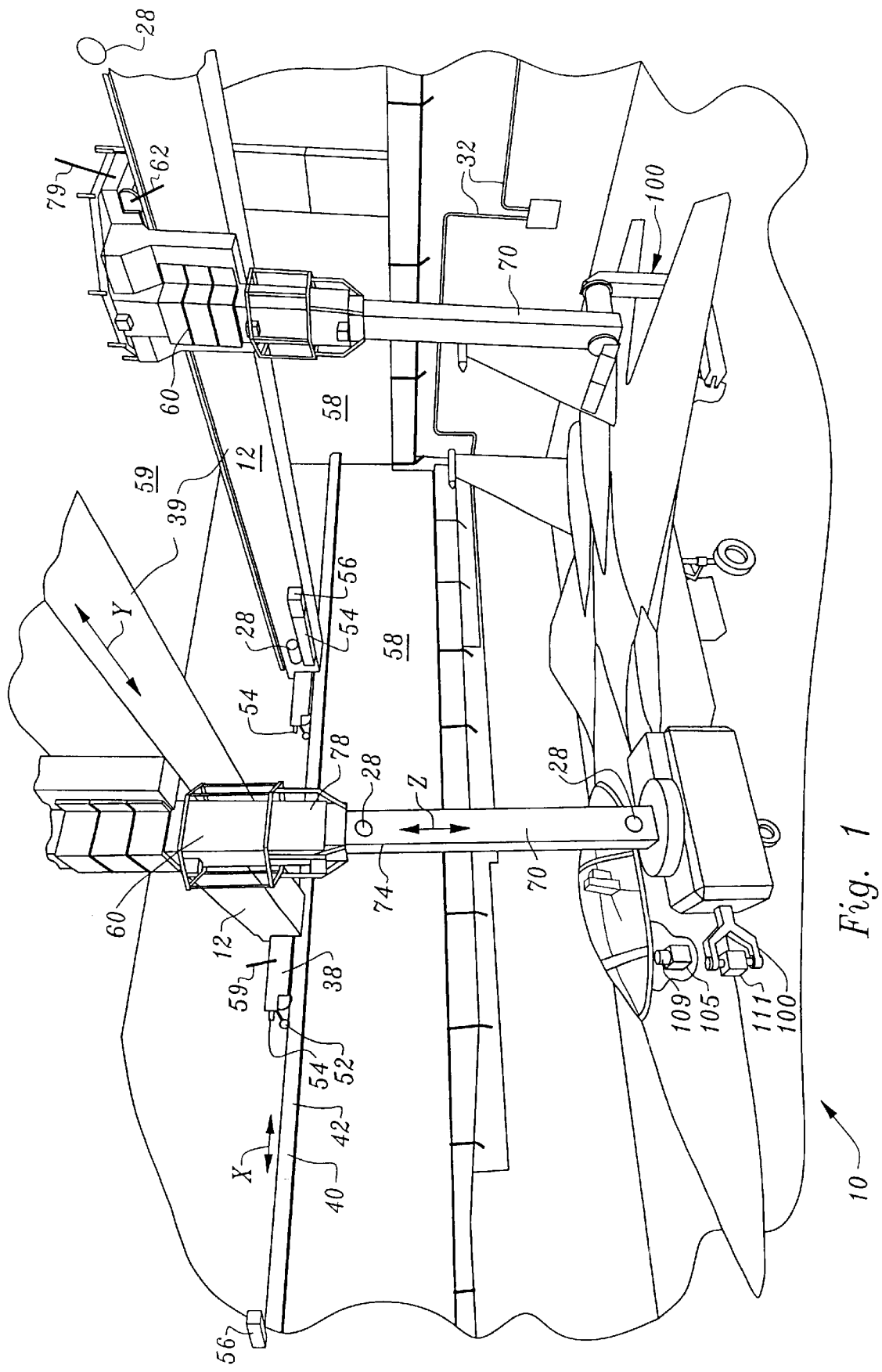
FIG. 1 is a perspective view of the system according to the present invention.

Considering the drawings, wherein like reference numerals denote like parts throughout the various drawing figures, reference numeral 10 is directed to the non-destructive inspection and testing system for aircraft components according to the present invention.

The Robotic Overhead Positioner (ROP), (e.g., FIG. 1) is a gantry robot that resembles an overhead crane. The ROP allows movement in three linear directions (X, Y, and Z) and three rotational directions (Yaw, Pitch and Roll to be described). Generally, to move in each of these directions, it uses a variable-speed DC motor 14 (FIG. 1A), a gearbox 16, and a drive mechanism 18 having wheels 52. Power to turn the motor (thus moving the robot) is supplied by a controller 20. Each motor 14 has an encoder 22, which tells the controller 20 the distance of travel; and it also has a solenoid energized electric disc brake 24, which keeps the robot in a frozen position whenever the controller 20 is not supplying power to the motor 14. For each direction the robot 12 can move, there is also an absolute-positioning resolver 26, which tells the controller 20 where the robot is via the encoder 22. Limit switches 28 inside the resolver 26 prevent the motors 14 from driving the wheeled drive mechanism 18 beyond its end of travel. Power to the motors 14 and signals to the controller 20 are supplied via cables 32 (FIG. 1), which are fully insulated and which have military-standard connectors. Heavy-duty frictionless bearings 36 are used throughout to maximize system reliability.

Specifically, in the first linear direction (X-axis) (FIG. 1 and FIG. 1A) the bridge 38 moves on the runway 40. The runway 40 is made of sets of two parallel rails 42 (FIG. 2) mounted on rail ledges 44 (FIG. 2A). FIG. 2 shows one rail 42 on each sidewall 46 (and two rails 42 on the central corbel 43) of the Inspection Bay 48; these rails 42 have adjusters 50 for leveling and parallel alignment. Please see FIG. 2A.

The wheels 52 support bridge end trucks 38, a pair of wheels 52 on each end, and ride on the rails 42. Each pair of wheels has its own motor 14 and its own resolver 26. The bridge 38 encloses and supports the drive mechanism 18. As the motors 14 turn, the wheels 52 turn, moving the bridge 38 back and forth on the rails 42. The dual motor 14/resolver 26 scheme enables the controller 20 to avoid the bridge 38 skewing off the rail 42. If the limit switches 28 in the resolver 26 were to fail, thereby allowing the operator to move the bridge 38 to the very end of the rails 42, shock absorbers 54 on the bridge 38 and end-stops 56 on the rails 42 prevent the bridge 38 from striking the walls 58. A crank 59 is provided on each end of the bridge 38 as a manual backup motion system to allow the bridge to move without the motor 14.

Figures 1A, 2A:
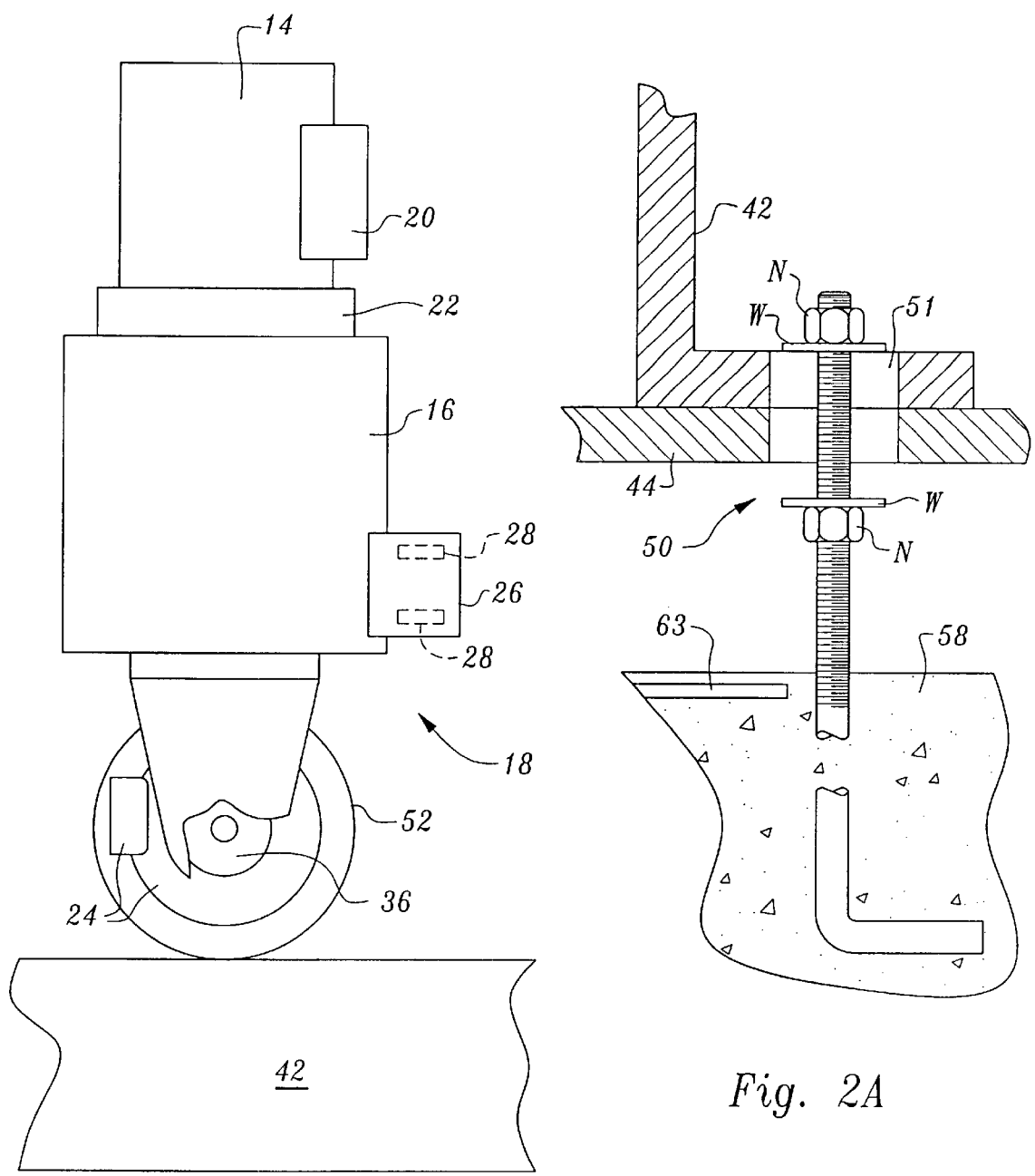
FIG. 1A details one robotic movement system.
FIG. 2A details attachment of the FIG. 1A rail.
Figure 2:
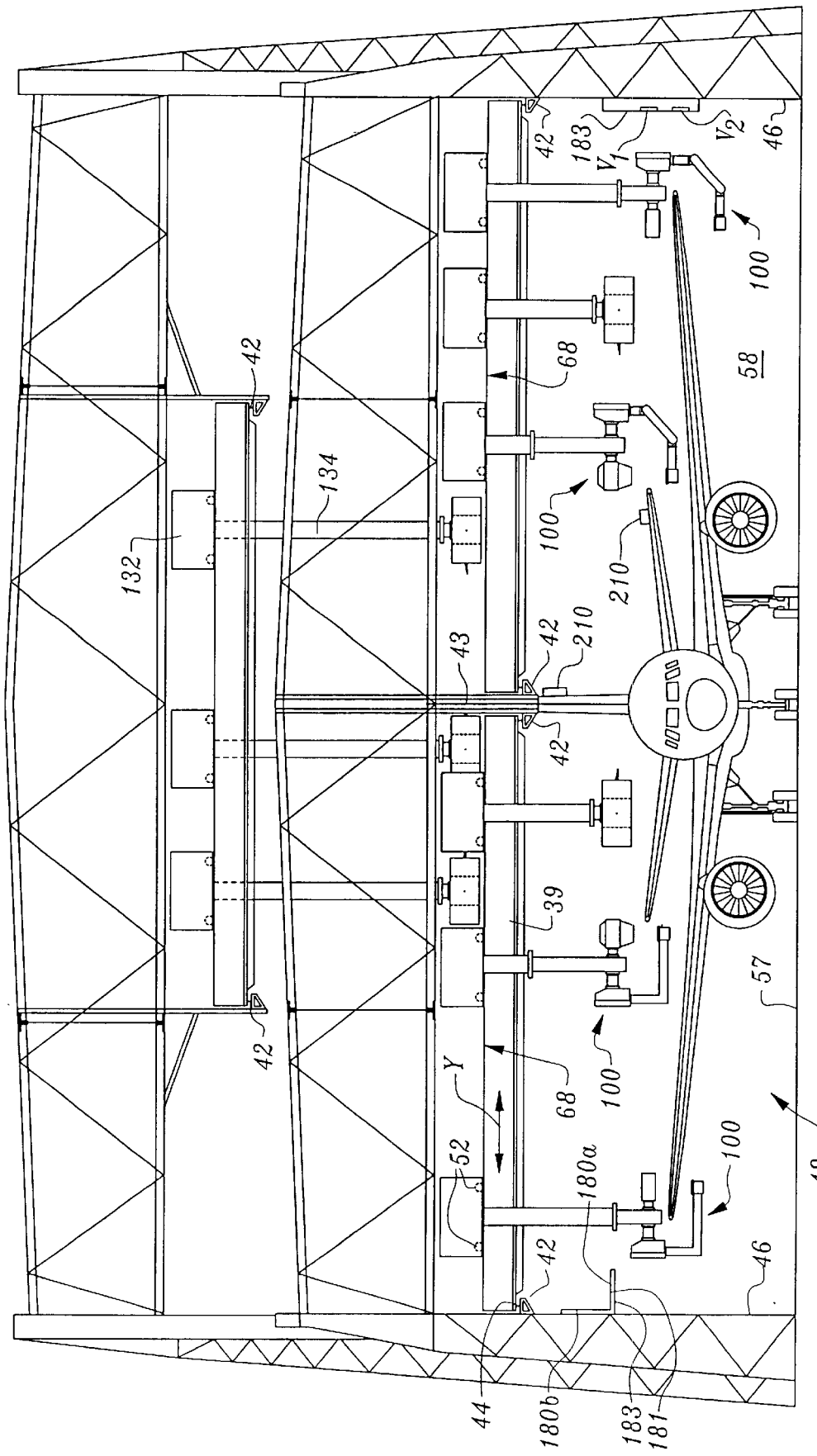
FIG. 2 is a front view of FIG. 1 for a different airplane.
Figure 3:
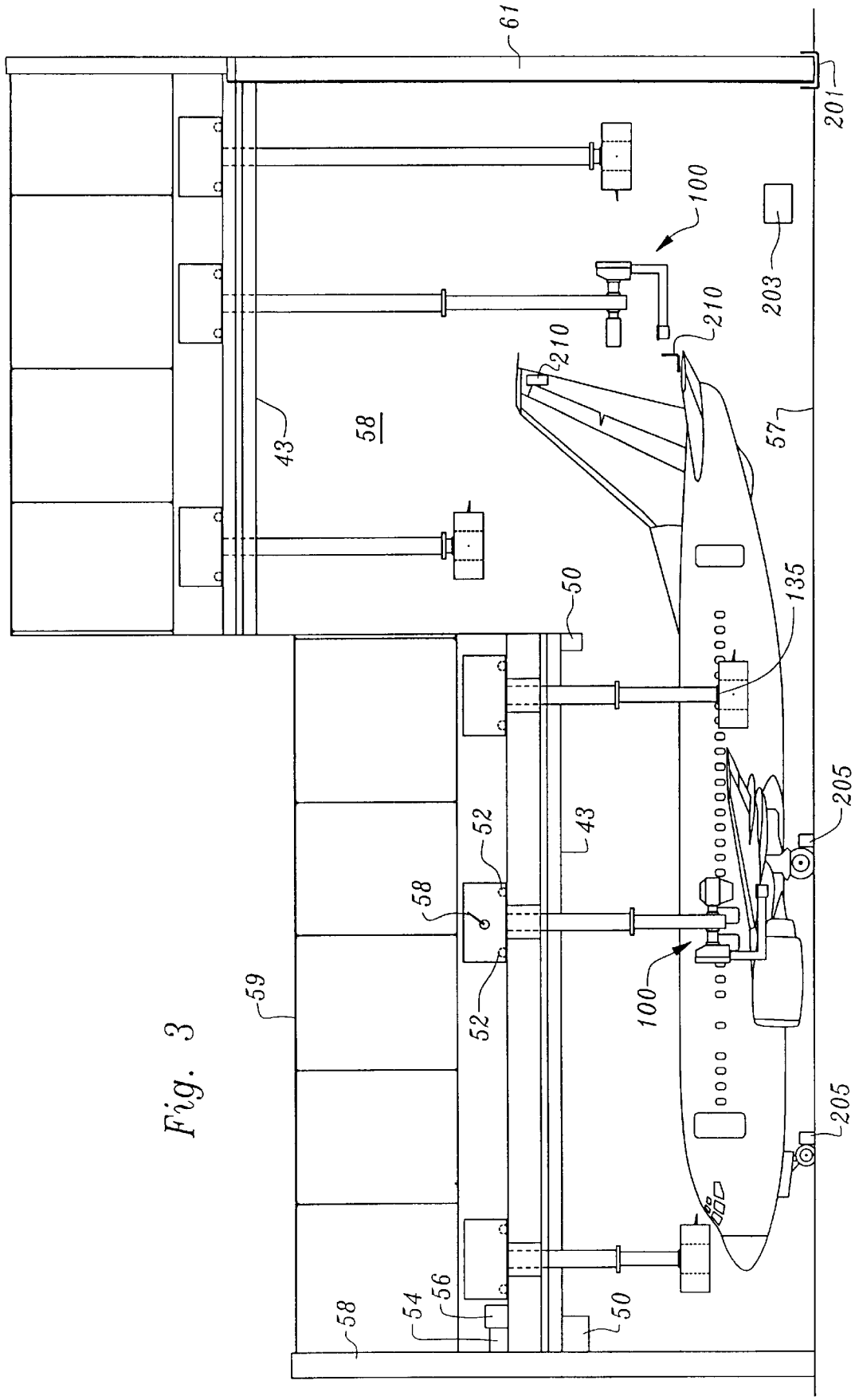
FIG. 3 is a side view of FIG. 2.
Figure 3A:
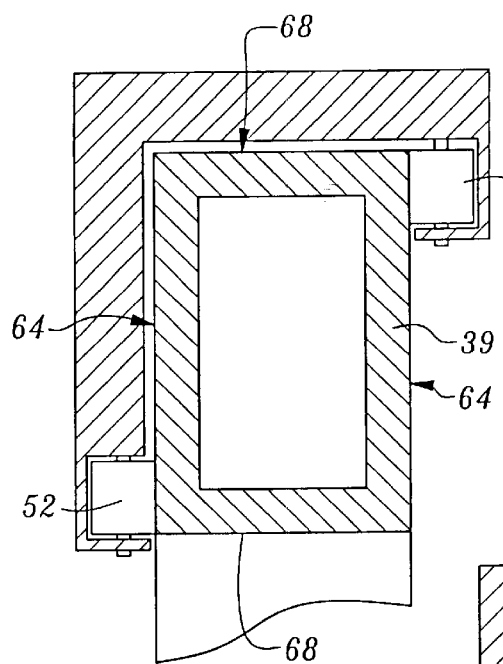
FIG. 3A details a vertical mast support.

FIGS. 1 and 2 show the second linear direction (Y-axis) where the trolley 60 moves along a span 39 which extends between two rails 42. Similar to the X direction, a trolley 60 moves along span 39 in depending relationship. Please see FIG. 3A. The span 39 is box-shaped and has spaced parallel vertical rails 64 and spaced parallel horizontal rails 68 forming an enclosed box. The weight of the trolley 60 is bearing on its wheels 52 that ride on opposed outer faces of each vertical rail 64. As the motor 14 turns, the wheels 52 turn, moving the trolley 60 left and right (Y axis) on the span 39. One wheel set 52 rides on a lower edge of one vertical rail 64 and another wheel set 52 rides on a top edge of opposite vertical rail 64 to keep the trolley 60 (and thus the mast 70) from tilting. The span 39 preferably has an upwardly projecting central crown 68 (FIG. 2) of about one-half inch when unloaded and bows one-half inch downwardly when the trolley 60 moves to the middle of the span 39. Thus, the span 39 is therefore normalized (i.e., level) along the length. If the limit switches 28 in the resolver 26 were to fail, allowing the operator to move the trolley 60 to the end of the rails 42, shock absorbers 54 on the span 39 and end-stops 56 on the span's ends prevent the trolley 60 from striking the walls 58. A crank 62 is provided on each trolley 60 as a manual backup system to allow reorientation of the trolley 60 along span 39. The trolley's drive is similar to that shown in FIG. 1A.

Figure 4A:
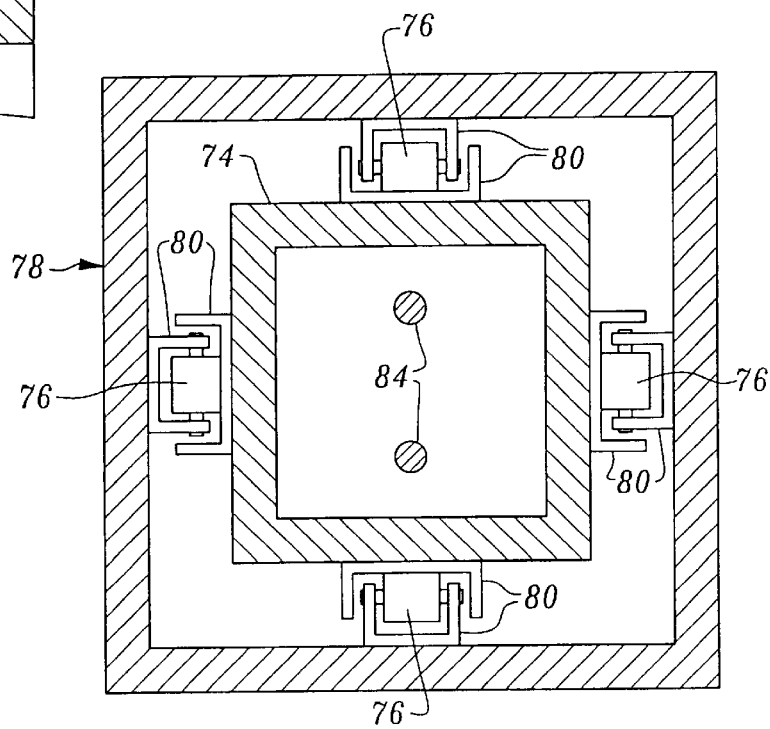
FIG. 4A is a section of the mast.
Figure 5A:
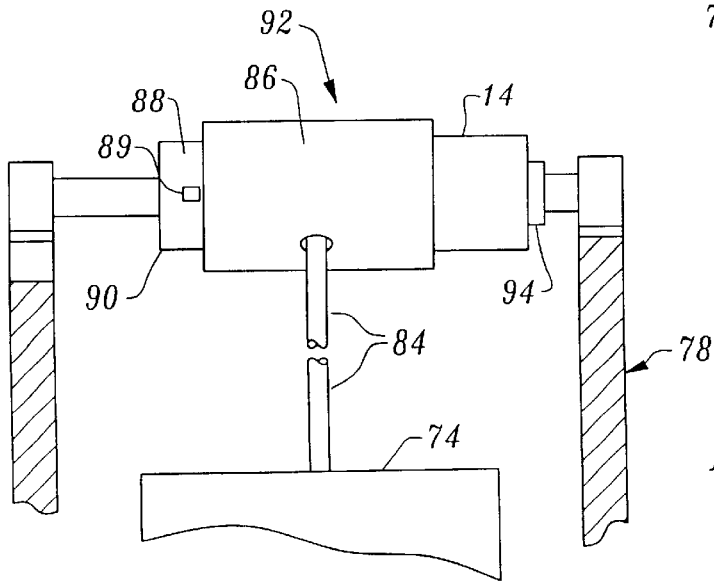
FIG. 5A is a view of the mast drive system.
Figure 4:
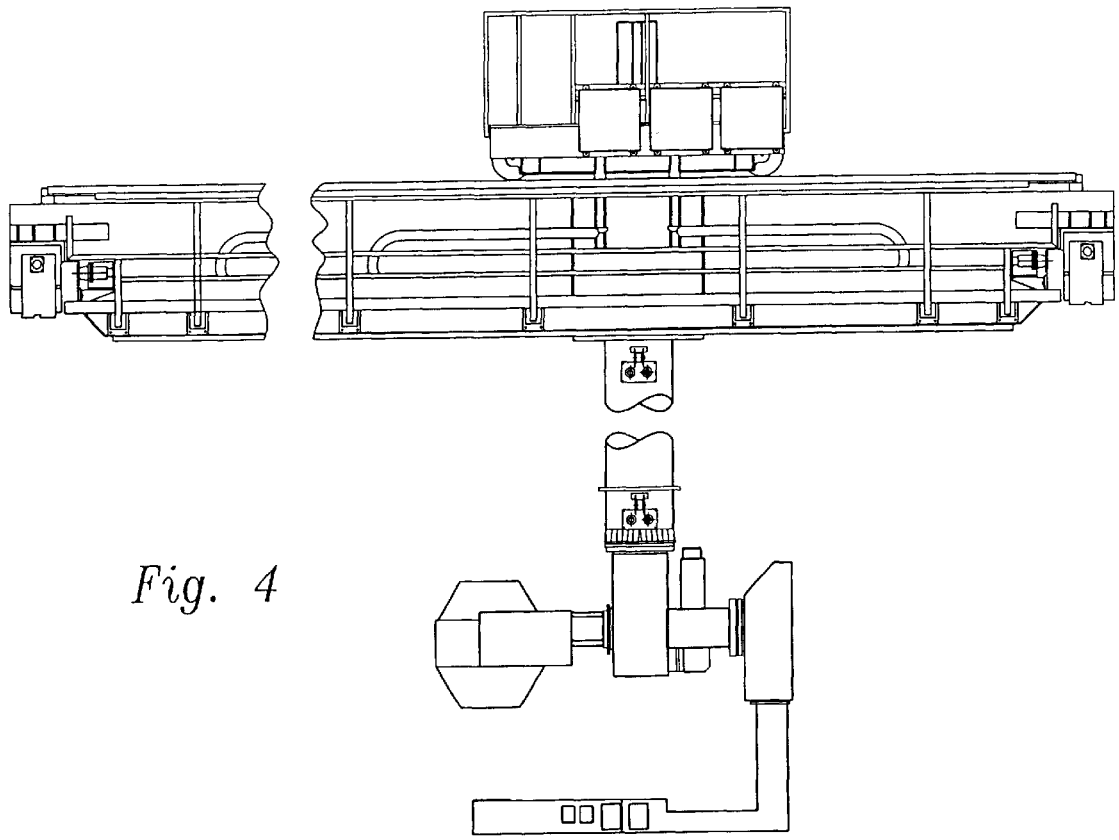
FIG. 4 is a top view of the N-Ray system.
Figure 5:
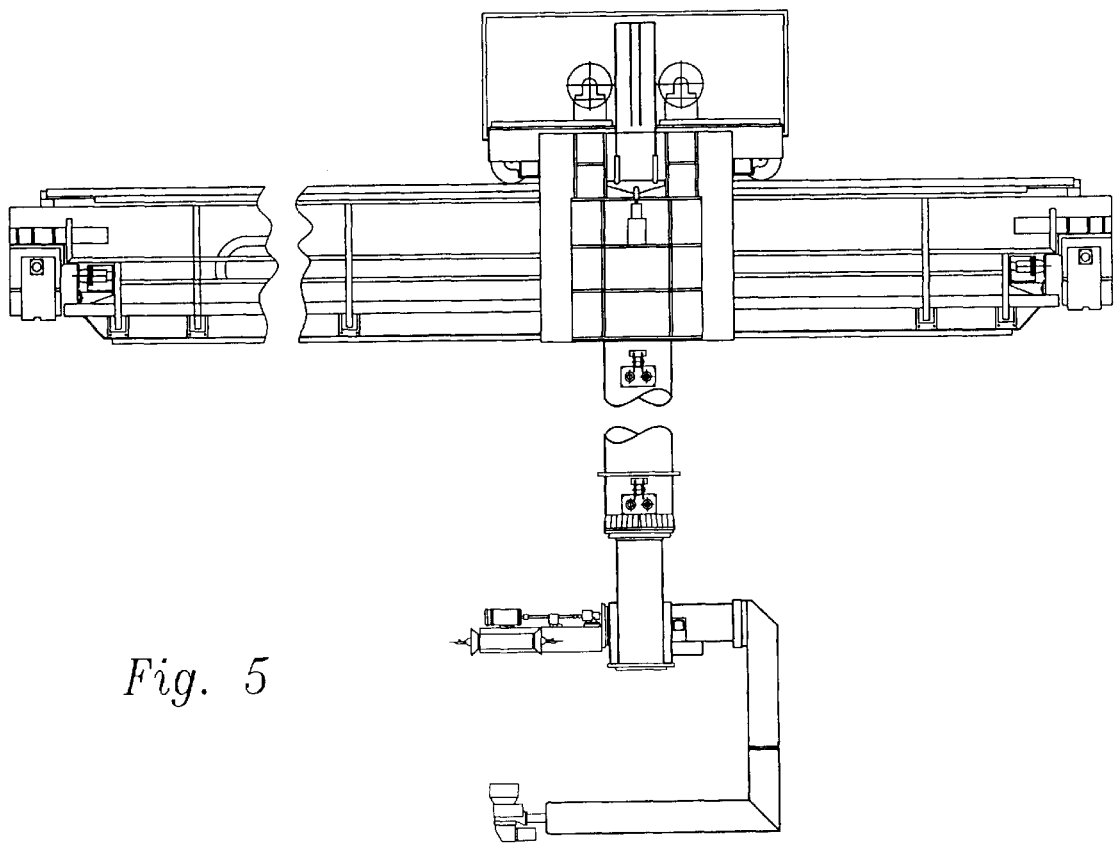
FIG. 5 is a top view of the X-ray system.

The third linear direction (Z-axis) moves the mast 70 on the trolley 60 up and down via positioner 92, please see FIG. 5A. The mast 70 is preferably capable of hoisting at least 5000 pounds, and is designed such that the failure of any single part of the system will not cause its sensor array (to be described) at the free end of the mast 70 to fall to the bottom of mast travel. As seen in FIG. 4A, the mast 70 is a box-shaped inner telescoping tube 74 with wheels 76 on an inner surface of box-shaped outer tube 78 riding on rails 80 on the inner tube 74. As seen in FIGS. 4A and 5A, the mast 70 is hoisted by dual cables 84 and has two drums 86 (only one shown); as the motor 14 turns, each drum 86 deploys a cable 84, hoisting the inner tube 74. Each drum 86 has a brake 88 mounted to its drive shaft 89 to prevent the tube 74 from falling if one brake 88 should fail. A load sensing mechanism 90 embodied as an overload clutch is provided on the hoisting system brake 88 to stop the mast if a sensor supporting yoke 100 (e.g., FIG. 2) should catch on an object as it is hoisted up or down or if there is a system overload. This load sensing mechanism 90 will also stop the positioner 92 when one component of the hoist system quits operating. For a backup system, each cable/drum system is capable of hoisting the mast at full load. If the hoist were to over-speed, another sensor 94, monitoring amperage would again perform to trigger an emergency stop. A crank 79 (FIG. 1) is provided on each mast 70 as a manual backup motion system.

Figure 6:
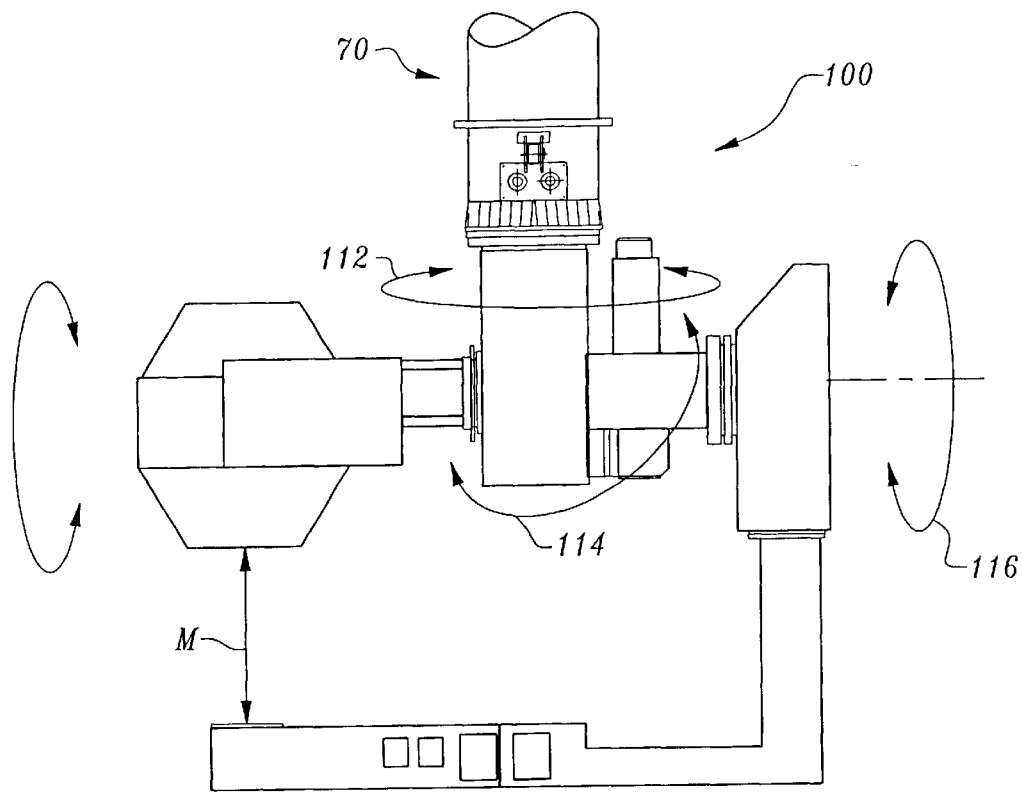
FIG. 6 is a side view of the N-ray yoke.
Figure 7:
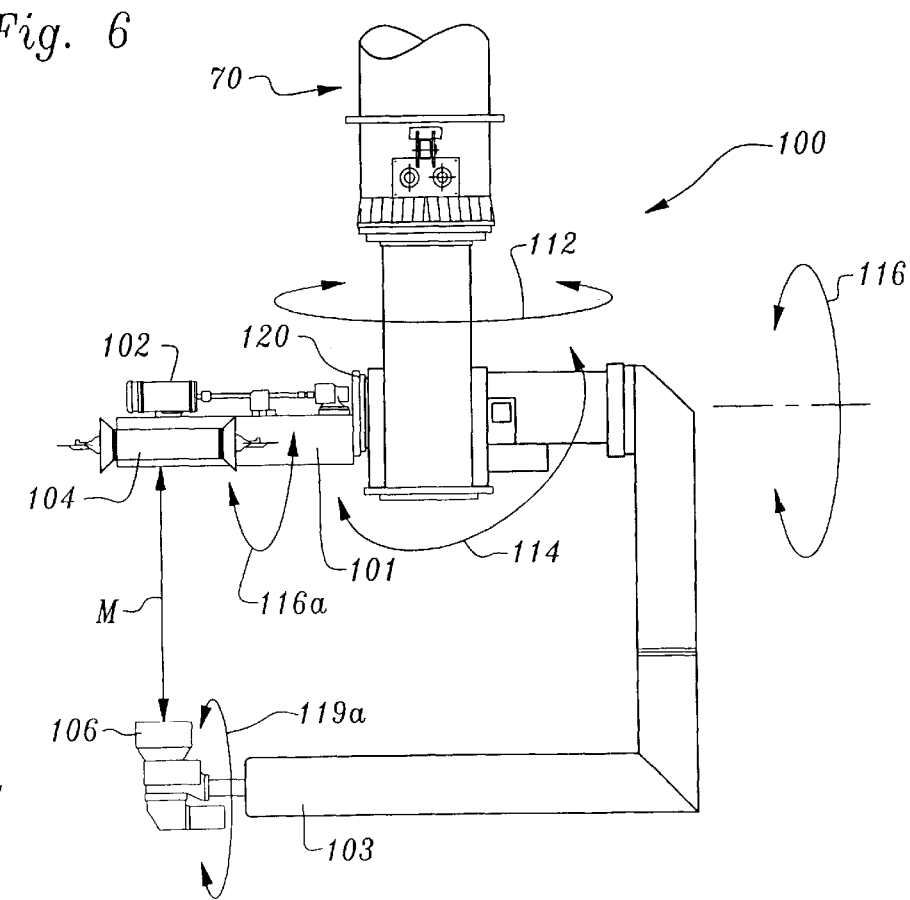
FIG. 7 is a side view of the X-ray yoke.
Figure 8:
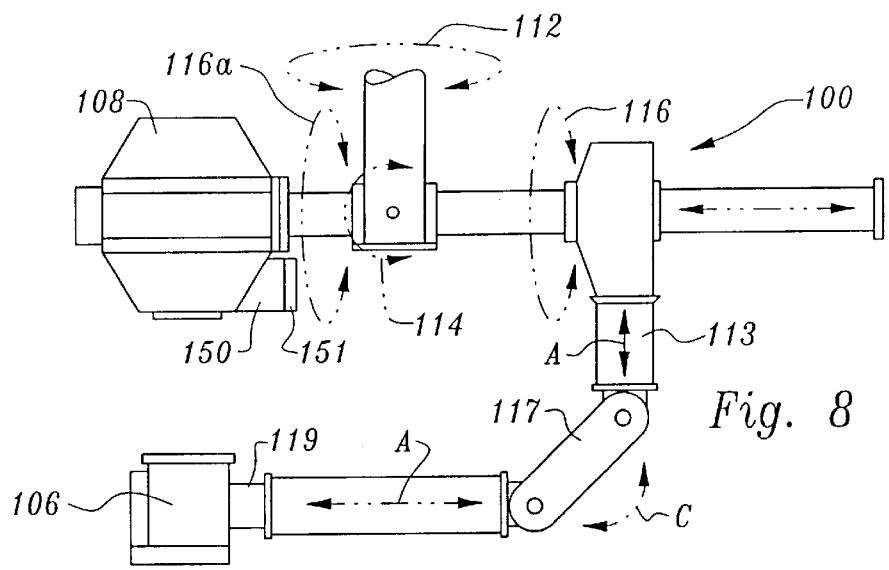
FIG. 8 is a side view of the N-ray yoke.
Figure 9:
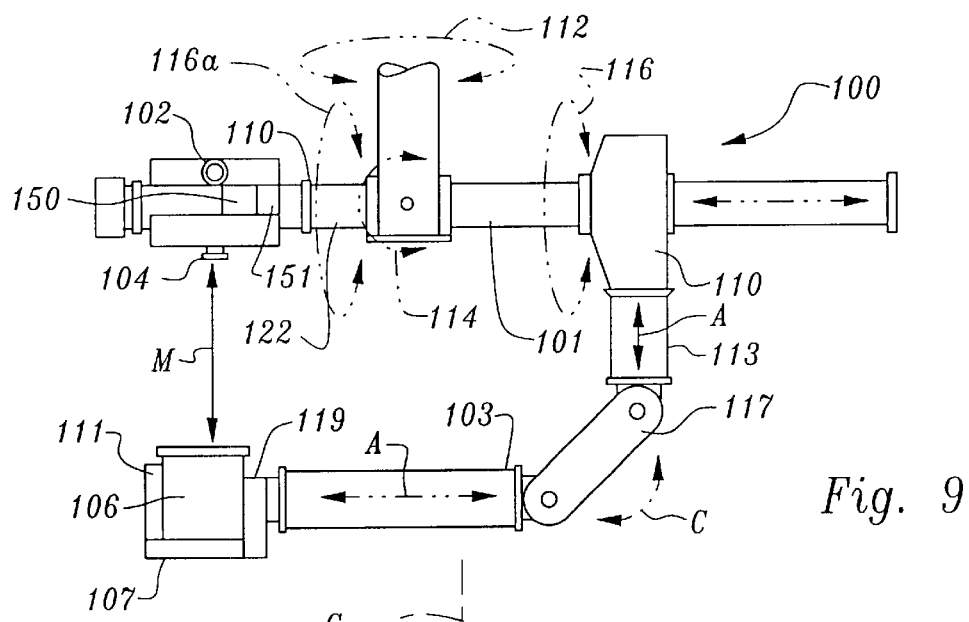
FIG. 9 is a side view of the X-ray yoke.

Three rotational axes are incorporated into each inspection yoke 100. Please see FIGS. 6 through 9. The yoke 100 is a C-shaped structure with an adjustable mouth M which spans the gap between the sources and receiver. Two X-ray sources 102, 104 (FIGS. 7 and 9), having differing outputs are mounted on the top support 101 of the yoke 100 and the image receiver 106 is mounted on the bottom by arm 103; the yoke 100 also supports a collision-avoidance paneling 110. The paneling is a pressure sensitive sheath and is mounted on all lower extremities of the mast 70. The pressure sensitive paneling prevents gross contact with the aircraft by mandating a stop signal in the presence of a triggering pressure. During the scanning of the aircraft surfaces, the surface (e.g. wing) is positioned between the X-ray 102, 104 (and N-ray 108, FIGS. 6 and 8) sources and the imager 106. A film source 107 may supplement or supplant the imager 106.

The first rotational axis 112 (Yaw) rotates the inspection yoke 100 in a horizontal plane at the bottom of the mast 70. The second rotational axis 114 (Pitch) pivots the inspection yoke 100 in a vertical plane at the bottom of the mast 70. The third rotational axis 116 (Roll) rotates the inspection yoke 100 in a plane at the end of the pitch axis; this plane is oriented perpendicular to the pitch axis. Note X-ray 102,104 and N-ray 108 can be independently rotated about 116a. Further, each arm (e.g. bottom arm 103, side arm) can change in length as shown by double ended arrows "A" in FIGS. 8 and 9. Also note that link 117 connecting bottom and side arms 103, 113 can rotate about curved arrow "C" to adjust the dimension of adjustable mouth M, in conjunction with the telescoping arm's length along arrow "A".

The X-ray sources 102, 104 are mounted on a movable support to allow only one of the two sources to be aimed at the imager 106 at one time by rotation about 116a. This support, called a turret 120 (FIG. 7), is rotated 90 degrees by a stepper motor 122 (shown schematically in FIG. 9). Only the X-ray source aimed at the imager 106 may be activated unless a permanent record is desired via a film source 107 which rotates in the place of imager 106. Alternatively, the film source 107 can rotate about axis 119 (arrow 119a, FIG. 7) to orient the film source 107 to the X-ray 102, 104. The X-ray sources 102, 104 are indexed into position as a function of the object being scanned, its thickness, and its composition (e.g. composition versus metal). The imager 106 is an image intensifier, which directs the X-ray image to the control room operator CRT screen. The bottom arm 103 may also carry another type of X-ray imaging system 111 for backscatter X-ray (reverse geometry X-ray). The sender unit 111 is shown mounted adjacent imager 106. Photomultiplier tubes 109 (FIG. 1) are positioned inside the aircraft to receive digital images from the sender 111. Receivers 105 are also placed on the inside of the production aircraft structures and direct digital imaging information to be sent to the control room operators. Yoke manipulative and imaging capabilities specified for either the N ray or X ray could be incorporated in the other.

Because of the varying change in the thickness of aircraft internal structures (such as wings), the X-ray source output (KVP Kilovoltage Penetrating Power, MA Milliamps Current) is controlled by robotic coordinates to allow ramp up or ramp down of X-ray penetrating power. This allows clear and precise imaging. It also allows the operator to focus attention to the viewed images and not constantly adjusting output due to the change in the aircraft structure material thickness. More importantly, each and every aircraft is inspected exactly the same (standardization).

The yoke 100 also contains a heat gun 150, somewhat like a hair dryer. This is used on both the X-ray and N-ray yokes to allow the operator to verify and distinguish the presence of moisture, water or fuel inside the aluminum or composite bonded structure. Current industry NDI or NDE methods cannot distinguish the difference between moisture and sealant. Once a defect area is detected by either the X-ray or N-ray inspection method, heat is applied by the yoke's heat gun 150 to that specific area. Heat out generation is monitored by an infrared pyrometer 151 in order not to exceed a limit, preferably 160 degrees F. on the structure where the heat is being applied. If moisture is present, the applied heat causes migration of the fluid away from the heat source due to expansion of the air within the heated structure area. Heat images are taken before and after heating. Alternate "before and after" images flash on the operator's CRT screen and image picture subtraction is accomplished. The difference allows the operator to watch moisture migration. This procedure is important in locating the water entry paths within the aircraft structure or component.

Figure 10:
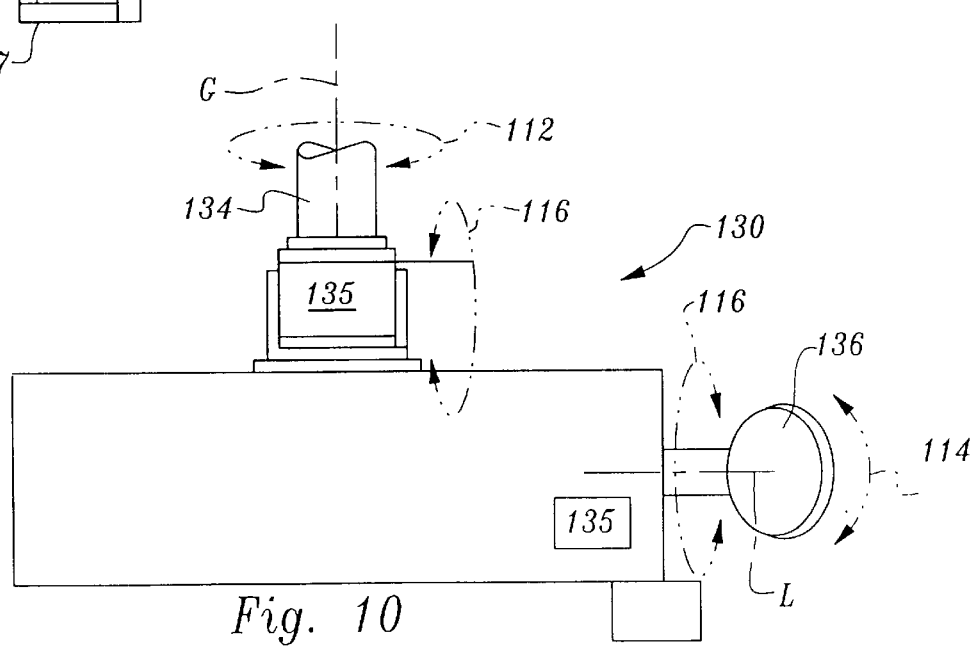
FIG. 10 is a side view of the laser yoke.
Figure 11:
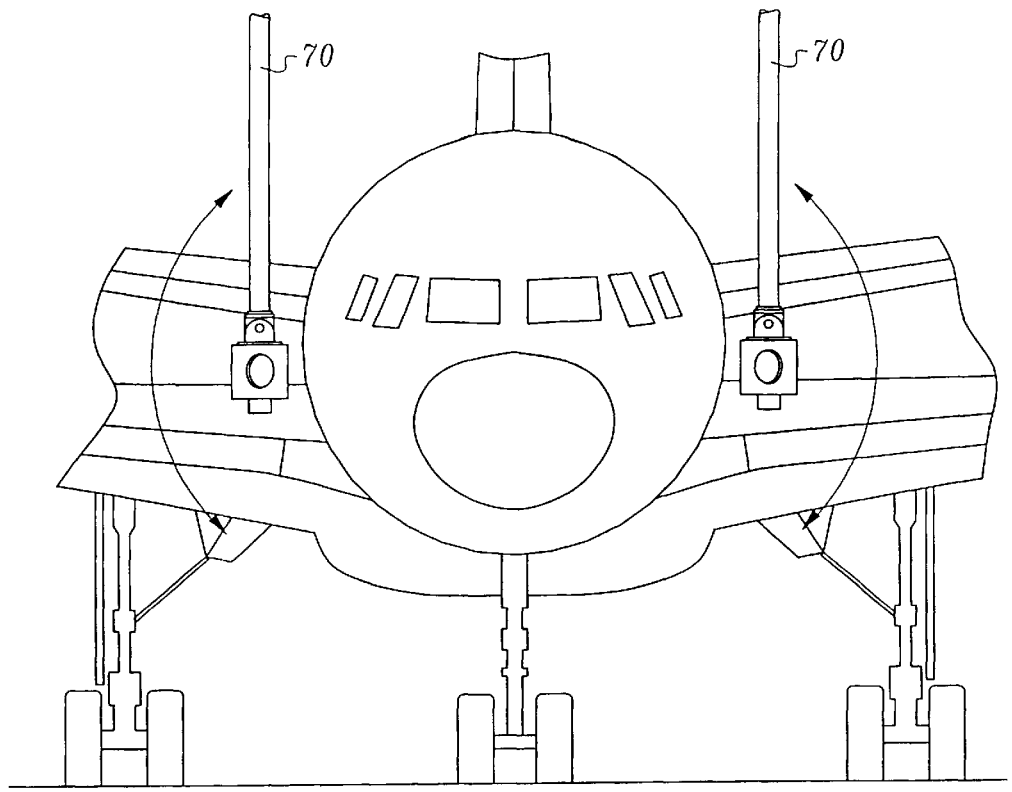
FIG. 11 is a front view of the laser addressing the plane.
Figure 12:
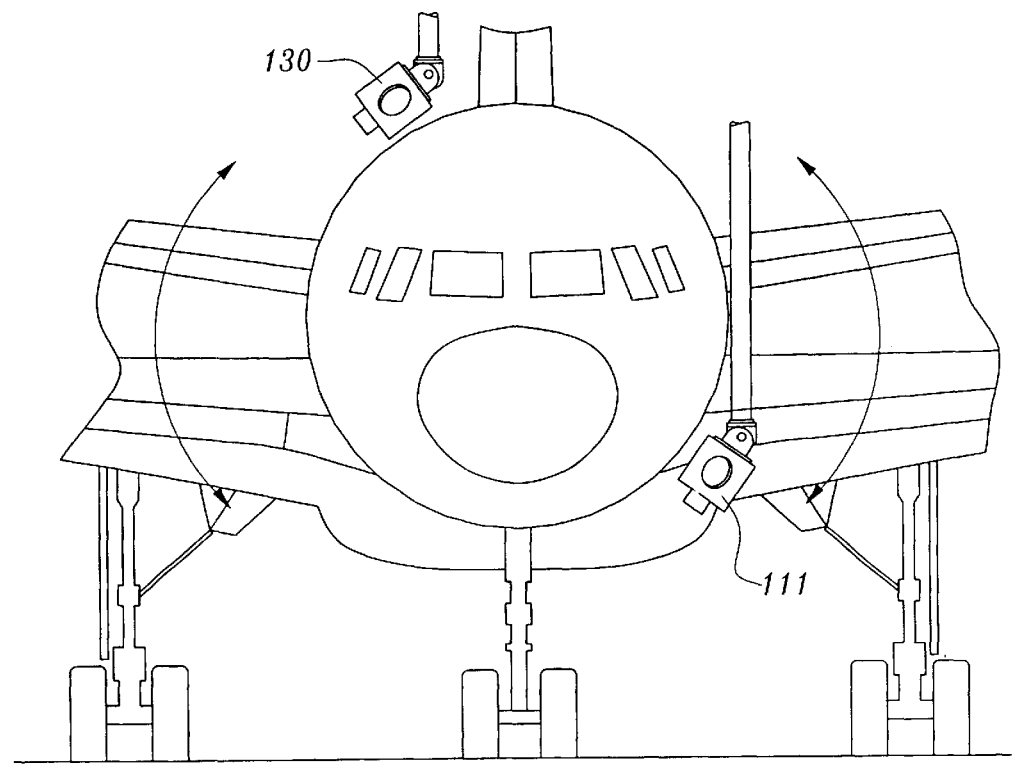
FIG. 12 is a front view of the laser addressing the plane.
Figure 13:
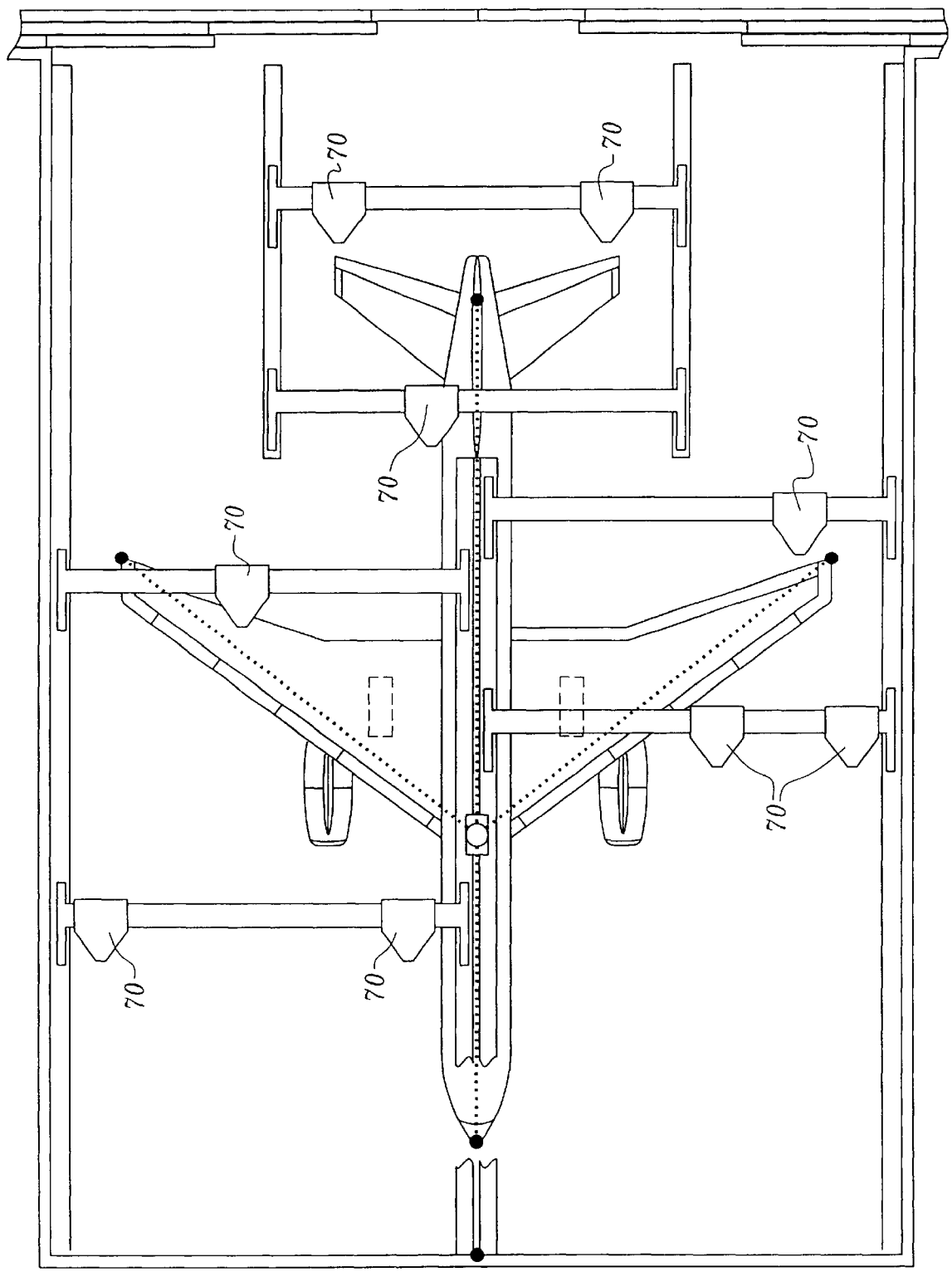
FIG. 13 is a top view of the system.
Figure 14:
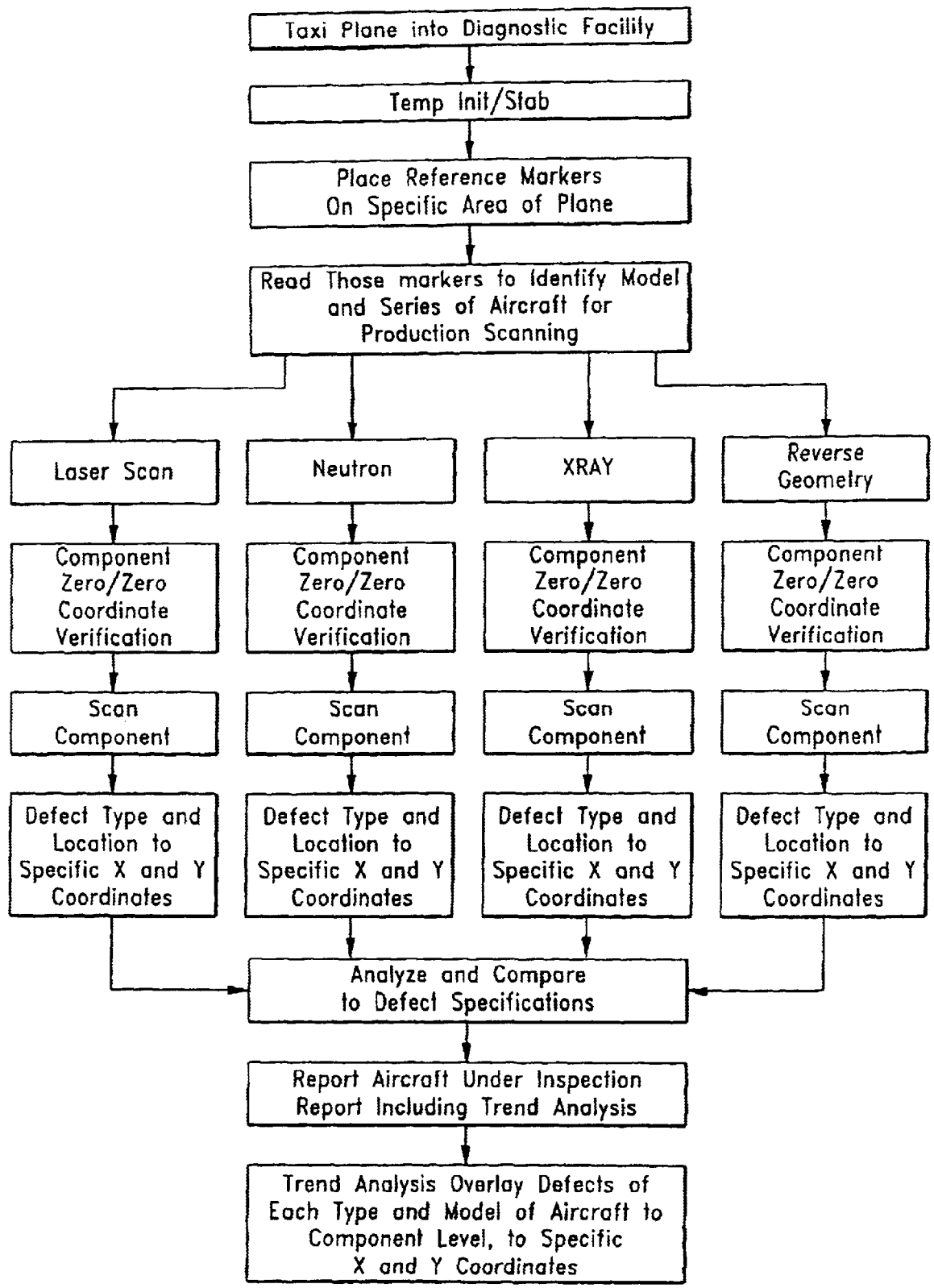
FIG. 14 is a flow chart for the system.

A laser ultrasonics apparatus 130 is also mounted to the gantry robot system 12. Like the yoke 100, the apparatus 130 (FIG. 10) is coupled a carriage 132 (FIG. 2) and a mast 134 mounted to the carriage 132 with rotational axes as described for the previous trolley and mast. The ultrasonic laser apparatus 130 allows X (along line L), Y (up and down along line G), and rotational movement (e.g. about arrows 112, 114, 116) by using stepper motors 135. The rotational movement of the laser ultrasonic apparatus allows it to reach underside areas of the fuselage while being support by the gantry robot system 12 that is above the fuselage. Please see FIGS. 11 and 12. A mirror 136 receives laser energy L from within housing 130 and distributes the energy on the scanned surface by mirror rotation, indexing and mast rotation and scanning (FIG. 12). Reflected laser light provides further diagnostics.

Each individual robot has a "home" position to verify accuracy and to correct possible relocated robot movement (such as from earthquakes). An example of this is the home position fixture for the X-ray and N-ray inspection system. The home position fixture is preferably inverted "L" shape flat plate steel 180 (FIG. 2) whose vertical leg 180b is attached to the wall 46 with approximately four feet overhang provided by horizontal leg 180a from the wall. The flat steel plate overhang horizontal leg 180a is parallel to the concrete facility floor. A small 0.030-inch hole 181 is drilled through the center of the overhang plate 180a. With the X-ray system on, the operator CRT screen contains crosshairs (like a hunting rifle scope) to locate the crosshairs in the center of the overhang 0.030-inch hole at 5×geometric magnification. This provides a home position initialization step (calibration) and is preferably performed prior to each and every aircraft inspection and also for all robots and each inspection method (X-ray, N-ray and Laser Ultrasonics). Laser alignment relies on a uniform thickness plate 183 having at least two variations $V_1$ and $V_2$ from the uniform thickness at known locations. The laser when scanning the variations (e.g. a counter-bore) should reflect the known variations as a function of relative length and distance. In FIG. 2A, rails 42 can be aligned by oval slots 51 allowing motion of rail 42 relative to its support plate 44. A J bolt supports rail 42 and plate 44 in wall 58. A threaded free end of J bolt 50 includes washers W and nuts N for vertical and lateral truing.

As previously stated, the present invention has at least one and preferably three or more robots. The use of multiple robots provides several advantages. Firstly, multiple robots allow simultaneous inspection of several areas of an aircraft, thereby reducing the time required to inspect an aircraft.

Secondly, multiple robots avoid the need for a single long supporting beam, which would reduce positioning accuracy and repeatability. Thirdly, multiple robots allow each robot to be specifically designed to inspect particular areas of an aircraft, thereby allowing accommodation of special attributes of the various areas.

Corbels 12, 43 and rails 42 are provided to support multiple robots. The walls 58, ceiling 59, and hanger door entrance 61 are designed to support the corbels and rails, which permit linear translation. The location of the corbels within the structure, e.g., an aircraft hanger, is designed to accommodate structural loading (due to weight of the robot, robotic movement yielding unaccepted resonate frequencies, etc.) while maintaining accuracy and repeatability of robot position over six axes of movement within a narrow range of tolerances to ±0.160 inches. The structure accommodates structural loading of various types, for example floor loading, wind loading and loading from the mass of the robots.

The inspection facility is designed to protect personnel from radiation hazards (including X-rays and neutrons). Shielding 63 (FIG. 2A), including shielding of walls, doors, and windows is provided. Interlocks 201 (FIG. 3) are provided to prevent the emission of radiation when personnel might be endangered, such as when a door is opened. Other measures, such as key controls and password authentication are provided to prevent emission of radiation or other potentially hazardous activities, such as motion of robotic systems, without approval of authorized personnel. Radiation monitoring and alarm systems 203 are provided to detect abnormal radiation levels and provide warning.

One example of a technique used to provide radiation safety even though the walls, doors, ceiling and viewing windows are designed to accept maximum radiation at a distance of three feet, is not allowing the X-ray or N-ray sources to be aimed at these surfaces. The robot positioners only allow the radiation source to be aimed toward the concrete bay floor 57, or aircraft structure. This is accomplished by programming the robotic movement throughout the facility. Other than in the scan plan during the aircraft inspection operation, the radiation sources are non-operational. This is called the "Robotic Approach." Both X-ray and N-ray sources are on/off systems; neither source can be energized other than at the beginning of the scan plan inspection operation or calibration. Override of this radiation protection system is accomplished for robot or source maintenance purposes only and controlled by software code known only to the first level supervisor and maintenance personnel.

A method for design of a non-destructive inspection, testing and evaluation system for aircraft component having a precision robotic system is provided. The dimensional and structural requirements of a building are determined, and a preliminary design for the building is made. The preliminary design for the building is analyzed to identify any frequencies (earthquake zones) at which such a building might resonate. For example, a technique such as finite element frequency analysis may be employed. Based on the results of the analysis, the preliminary design of the building may be modified to correct any deficiencies.

The dimensional, structural, and functional requirements for robots to be housed within the building are determined, and a preliminary design of the robots is made. The preliminary design of the robots is analyzed to identify any frequencies at which such robots might resonate. Any interaction between the resonant frequencies of the building and the resonant frequencies of the robots are analyzed. Based on the results of the analysis, the preliminary design of either or both of the building and the robots may be modified to correct any deficiencies.

The dimensional, structural, and functional requirements of any end effectors mounted on the robots are determined, and a preliminary design of the end effectors is made. The preliminary design of the end effectors is analyzed to identify any frequencies at which such end effectors might resonate. Any interruption between other elements, such as the building or the robots, is analyzed. Based on the results of the analysis, the preliminary design of any or all of the building, robots, or end effectors may be modified to correct any deficiencies.

Another factor to be considered is the type of earthquake region in which the facility is to be located. Different earthquake regions may exhibit earthquakes having different characteristics, for example earthquakes have vibration and motion of predominantly a certain frequency range. This frequency range is determined for the location at which the facility is to be located based on geological data. The preliminary designs of the building, robots, and end effectors are analyzed base on anticipated excitation from earthquakes. Based on the results of the analysis, the preliminary design of any or all of the building, robots, or end effectors may be modified to correct any deficiencies.

When the preliminary designs of the buildings, robots, and end effectors are completed, modeling of the entire system may be performed to assure accuracy and repeatability of robot positioning. Oscillatory excitation of the system components resulting from robot motion and acceleration and deceleration may be analyzed. Designs of the system components may be modified to maximize desirable characteristics, such as accuracy and repeatability of robot positioning, while minimizing undesirable characteristics, such as unwanted oscillatory excitation of system components.

An NDI, NDT or NDE system or process having the characteristics of the present invention preferably contains the steps to perform the method for the non-destructive inspection and testing of aircraft intact or components including a database comprising at least one profile of a prototypical aircraft or component (a comparison standard), maintaining an enclosure at constant environmental conditions as to temperature, humidity, pressure, etc., and placing at least one aircraft or component into the enclosure for comparison with the standard.

A "gold body" database (i.e., a standard) is established for each configuration of aircraft such as the Boeing 727, 737 or 757. Also the length and height of the aircraft may vary and is identified by model and series such as the Boeing 737-100 or 737-400. Each model and series aircraft is located to a specific spot for the nose gear and main landing gear tires centerline and lined on the floor. Other production inspection aircraft of the same model and series will also use the line on the floor for rough positioning. The aircraft is then jacked into position using jacks 205 (FIG. 3) taking the load off of the tires and actuators. Thus, the aircraft becomes fixed in position and can no longer move due to tire pressure changing because of environmental changes or loss of hydraulic pressure in the actuators. Vision edges 210 (FIGS. 2 and 3), with two straight metal edges, 90 degrees to each other are attached to the aircraft's wing tips; horizontal stabilizer, outer leading edges and/or to other parts of the aircraft. The location of these vision edges are checked against the standard for initializing the system and to identify the type and model of aircraft to be inspected and also detect gross distortion and torsion of the airframe to be inspected. Thus, the vision edges define reference markers.

Each robotic imaging system such as the N-ray, X-ray and Laser Ultrasonics has a vision system, which allows the robot the ability to locate the aircraft within the robotic envelope. Scan plans are taught to each robot. For example, the X-ray robot is taught the angle of attack to inspect the wing internal structure for cracks such as in the inspection of the wing ribs and spars or taught to inspect the bonded structure on the same wing such as the leading edge, spoilers or flaps. Each scan plan is broken down to the aircraft component or panel level. Each component or panel has its own beginning point for a particular scan. This is known at the zero-zero coordinates. Defects are noted within the component or panel to exact X and Y-axis part coordinates for follow-on repair purposes or for tracking the defect growth over time.

Scan plans are different for each robotic imaging method such as for N-ray, X-ray or Laser Ultrasonics because of the field of view and the area of interest due to the type of aircraft structure. Nonetheless, the X and Y-axis coordinates on the component or panel remains the same. This allows the results of each inspection method (X-ray, N-ray, Reverse Geometry and Laser Ultrasonics) to be identified on a master layout; over laying the results of the inspections to identify multi-site damage and to download the results of each aircraft inspected to overlay on the same component or panel for determining trend analysis and model aircraft fleet condition.

Once the whole aircraft has been taught to the system of the present invention, the scan plans of each NDI method can be applied in part or whole on follow-on aircraft to be inspected (production aircraft). Production aircraft are not absolutely required to be jacked in place for stabilization. The aircraft is located within the facility to the line markings on the floor plus or minus eight inches. The robot then seeks to locate the vision edges on the aircraft. Once located, the robot automatically recognizes where the taught aircraft was in reference and where follow-on production aircraft is located. This is called an offset and is transparent to the system operators. Scan plan accuracy is 0.160 thousands of an inch on all production aircraft. Because no two aircraft are exactly the same, the system operator can manually align the robot by joystick control to the beginning zero-zero coordinates on each and every component, allowing 0.160 thousands of accuracy of scan for each component from aircraft to aircraft.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An apparatus for intact testing of aircraft, comprising, in combination:
    means for scanning the intact aircraft, said scanning means mounted on a robot, said robot free standing with respect to the aircraft; and
    comparison means to correlate data from the scanning means to a standard.

2. The apparatus of claim 1 wherein said scanning means includes means to move in three linear directions and about three axes.

3. The apparatus of claim 1 further including means to align said robot relative to the aircraft.

4. The apparatus of claim 3 wherein said means to align comprise reference markers located on the aircraft.

5. The apparatus of claim 1 wherein said robot includes a scanning head with means to move in three linear, orthogonally offset directions and three rotational directions.

6. The apparatus of claim 1 further including collision—avoidance means on said scanning means to prevent gross contact with the aircraft.

7. An apparatus for intact testing of aircraft, comprising, in combination:
    means for scanning the intact aircraft mounted on a robot; and
    comparison means to correlate data from the scanning means to a standard wherein said scanning means includes ultrasonics further including a structure configured to contain said apparatus and said aircraft under inspection, and with shielding to attenuate emissions or radiation to the outside of said structure;
    said apparatus is coupled to said structure, resulting in the formation of a gantry for supporting a carriage, a mast mounted on said carriage and at least one of an electromagnetic radiation emitter and electromagnetic radiation detector mounted on said mast which forms in part at least one radiographic inspection robot capable of precise positioning over large ranges of motion;
    said at least one radiographic inspection robot further comprises a beam structure for supporting and allowing horizontal translation of said carriage;
    said carriage is coupled to said mast, wherein said mast supports and allows a vertical translation of said at least one electromagnetic radiation emitter and detector mounted on said mast, and wherein said mast structure is configured to provide yaw movement of said at least one electromagnetic radiation emitter and detector; and
    said at least one electromagnetic radiation emitter and detector is configured to provide rotation about at least one axis of pitch, roll and yaw motion of said at least one electromagnetic radiation emitter and detector.

8. The system of claim 7 wherein said at least one of electromagnetic radiation emitter and detector is configured to a yoke to provide rotation about at least one of axis of pitch and roll motion of said at least one of electromagnetic radiation emitter and detector;
    said yoke includes first and second members capable of adjusting distance between said members;
    said first member supports a beam source; and
    said second member supports at least one of a beam detector or an imaging device.

9. An apparatus for intact testing of aircraft, comprising, in combination:
    means for scanning the intact aircraft mounted on a robot;
    comparison means to correlate data from the scanning means to a standard wherein said scanning means includes ultrasonics further comprising a hanger having a controlled environment, said hanger dimensioned to receive the aircraft therewithin;
    said robotic scanning means supported by said hanger and including means to move a scanning head of said robotic scanning means in three linear directions and three rotational directions;
    means to initialize said scanning head both with respect to said hanger and with respect to the aircraft; and
    means to correlate data derived from scanning the airplane to a standard.

10. The apparatus of claim 9 further comprising means to shield the hanger from radiation generated by said scanning head to prevent radiation from projecting there beyond.

11. The apparatus of claim 10 further comprising means to hold the plane in a constant position in said hanger.

12. The apparatus of claim 11 further comprising means to assess gross distortion of airplane geometry.

13. The apparatus of claim 12 further comprising said scanning head generating a laser scan.

14. The apparatus of claim 12 comprising said scanning head generating a neutron scan.

15. The apparatus of claim 12 comprising said scanning head generating an x-ray scan.

16. The apparatus of claim 12 comprising said scanning head generating a reverse geometry scan.

17. The apparatus of claim 1 wherein said scanning means includes n-ray.

18. The apparatus of claim 1 wherein said scanning means includes x-ray.

19. The apparatus of claim 1 wherein said scanning means includes reverse geometry.

20. The apparatus of claim 1 wherein said scanning means includes ultrasonics.

21. An apparatus for intact testing of aircraft, comprising, in combination:

means for scanning the intact aircraft said scanning means mounted on a robot;

a hanger having a controlled environment, said hanger dimensioned to receive the aircraft therewithin;

said robotic scanning means supported by said hanger and including means to move a scanning head of said robotic scanning means in three linear directions and three rotational directions;

means to initialize said scanning head both with respect to said hanger and with respect to the aircraft;

means to correlate data derived from scanning the airplane to a standard; and comparison means to compare data from the scanning means and the standard.

22. An apparatus for intact testing of aircraft, comprising, in combination:

means for scanning the intact aircraft, said scanning means mounted on a robot; and comparison means to correlate data from the scanning means to a standard;

further including a structure configured to contain said apparatus and said aircraft under inspection, and with shielding to attenuate emissions or radiation to the outside of said structure;

said apparatus is coupled to said structure, resulting in the formation of a gantry for supporting a carriage, a mast mounted on said carriage and at least one of an electromagnetic radiation emitter and electromagnetic radiation detector mounted on said mast which forms in part at least one radiographic inspection robot capable of precise positioning over large ranges of motion;

said at least one radiographic inspection robot further comprises a beam structure for supporting and allowing horizontal translation of said carriage;

said carriage is coupled to said mast, wherein said mast supports and allows a vertical translation of said at least one electromagnetic radiation emitter and detector mounted on said mast, and wherein said mast structure is configured to provide yaw movement of said at least one electromagnetic radiation emitter and detector; and said at least one of electromagnetic radiation emitter and detector is configured to provide rotation about at least one axis of pitch, roll and yaw motion of said at least one electromagnetic radiation emitter and detector.

* * * * *